(12) United States Patent
Lane et al.

(10) Patent No.: US 8,511,139 B2
(45) Date of Patent: Aug. 20, 2013

(54) SYSTEMS AND METHODS FOR IMPACT TESTING

(75) Inventors: Christopher Andrew Lane, Kitchener (CA); Cornel Mercea, Kitchener (CA)

(73) Assignee: Research In Motion Limited, Waterloo, Ontario (CA)

( * ) Notice: Subject to any disclaimer, the term of this patent is extended or adjusted under 35 U.S.C. 154(b) by 277 days.

(21) Appl. No.: 13/036,891

(22) Filed: Feb. 28, 2011

(65) Prior Publication Data

US 2012/0216596 A1 Aug. 30, 2012

(51) Int. Cl.
| G01M 7/00 | (2006.01) |
| G01N 3/00 | (2006.01) |
| G01N 33/00 | (2006.01) |
| G01P 15/00 | (2006.01) |

(52) U.S. Cl.
USPC .......................................... 73/12.13; 73/12.14

(58) Field of Classification Search
USPC ............................................... 73/12.13, 12.14
See application file for complete search history.

(56) References Cited

U.S. PATENT DOCUMENTS

| 3,999,420 | A * | 12/1976 | Wright .......................... 73/12.14 |
| 6,508,103 | B1 | 1/2003 | Shim et al. |
| 6,871,525 | B2 * | 3/2005 | Withnall et al. ............. 73/12.14 |
| 6,892,564 | B2 * | 5/2005 | Ishikawa ...................... 73/12.06 |
| 7,222,515 | B2 * | 5/2007 | Hatanaka et al. ............. 73/12.14 |
| 7,320,242 | B2 * | 1/2008 | Hoo Fatt et al. ............. 73/12.14 |
| 7,552,616 | B2 * | 6/2009 | Liu et al. ...................... 73/12.13 |
| 2004/0007047 | A1 | 1/2004 | Seung |
| 2005/0016256 | A1 * | 1/2005 | Ishikawa ...................... 73/12.13 |
| 2008/0105028 | A1 * | 5/2008 | Abke ............................ 73/12.14 |
| 2008/0178655 | A1 * | 7/2008 | Makimoto et al. ........... 73/12.14 |
| 2008/0289395 | A1 | 11/2008 | Torng et al. |

FOREIGN PATENT DOCUMENTS

| JP | 2000065678 A | * | 3/2000 |
| JP | 2004045335 A | | 2/2004 |
| WO | 8907176 | | 8/1989 |

OTHER PUBLICATIONS

Extended European Search Report; Application No. 11156188.2; Jul. 14, 2011; 7 pages.
Instron; Materials Testing Solutions; "Pendulum, Drop Weight and Instrumented Impact Testing"; http://www.instron.us/wa/applications/test_types/impact/test_types.aspx?ref=http://www.google.com/url; ; 2 pgs.
Advanced Test Equipment Rentals; "Shock Test Machine"; http://www.atecorp.com/Equipment/Avco/SM005_3.asp; ; 1 pg.
Instron; Materials Testing Solutions; "Pendulum Testers"; http://www.instron.us/wa/product/Instron-Pendulums.aspx?ref=http://www.google.com/url; ; 2 pgs.

* cited by examiner

*Primary Examiner* — Lisa Caputo
*Assistant Examiner* — Jamel Williams
(74) *Attorney, Agent, or Firm* — Conley Rose, P.C.; J. Robert Brown, Jr.

(57) ABSTRACT

A testing system having a retainer configured to selectively retain a specimen and a carrier configured to selectively carry the retainer along an at least partially predefined space curve from a first point along the space curve to a second point along the space curve, wherein a gravitational potential energy of the retainer at the first point is greater than a gravitational potential energy of the retainer at the second point. The retainer is configured to release the specimen in response to the retainer moving to a location that provides the retainer a predetermined gravitational potential energy.

20 Claims, 4 Drawing Sheets

SYSTEMS AND METHODS FOR IMPACT TESTING

BACKGROUND

Handheld portable telecommunication devices are prone to being dropped in a variety of situations such as during typical use, manufacturing, shipping and installation. The impact forces imparted to a dropped handheld portable telecommunication device may include a variety of device failures and/or inconveniences such as causing battery separation, component failure, solder-joint disruptions, display damage, and cracking and/or scuffing the outer casing.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with the full scope of equivalents.

Some impact testing systems are configured to test standardized material specimens by holding material specimens in a predetermined location and orientation while impacting the restrained and/or particularly situated material specimens. In some cases, such impact testing systems (i.e. Charpy testing systems and Izod testing systems) may not be amenable for use in testing complex test specimens, such as, but not limited to, handheld mobile telecommunication devices, that do not conform to the standards set forth for the standardized material specimens. Such test specimens may fail to conform based on the material composition and/or the physical dimensions of the test specimens. In some cases, using one of the above-described impact testing systems to test a non-conforming specimen may damage the impact testing system and/or result in the need to recalibrate impact testing system prior to reliably using the impact testing system for standardized material specimens. Further, the above-described impact testing systems may fail to adequately emulate a so-called drop test because, unlike a drop test, the impact testing systems may restrain a specimen during an initial and/or primary impact force and/or after such initial and/or primary impact force. Still further, such impact testing systems may typically be configured to test only one standardized test specimen at a time, thereby limiting a speed with which multiple specimens may be tested using a single impact testing system.

Additionally, while some impact testing systems (i.e., impact tables) may be capable of imparting known forces to a specimen, the systems may be prohibitively expensive to purchase, operate, and/or calibrate. Further, impact tables similarly fail to provide for free movement of the specimens during impact and immediately following impact. Still further, while some manufacturers, such as handheld mobile telecommunication device manufacturers, may implement a so-called drop test that comprises manually dropping a device from a specified height to determine the effects of the impacts on the device, the implementation of manually dropping a device does not allow a device to predictably receive an initial impact at predetermined location on the dropped device. Additionally, such drop tests may not allow sufficient reliability with regard to ensuring a particular predefined spatial orientation of the device when the device impacts an impact surface.

This disclosure provides systems and methods for overcoming one or more of the above-described disadvantages and/or shortcomings of some of the above-described impact testing systems and methods. For example, this disclosure provides systems and methods well suited for impact testing specimens that may comprise complex manufactured components and/or assemblies such as, but not limited to, handheld mobile telecommunication devices. Additionally, some embodiments of this disclosure allow a single impact testing system to test multiple specimens substantially simultaneously. In some embodiments of this disclosure, a location on a specimen may be reliably predetermined to receive an initial and/or primary impact. In some embodiments, the systems and methods may be relatively inexpensive and may require little or no calibration. Accordingly, in some embodiments of this disclosure, systems and methods for impact testing specimens may provide increased repeatability with respect to reliably providing a test specimen with a predefined spatial orientation relative to an impact surface and may further provide for simultaneously testing a plurality of test specimens.

Figure 1:
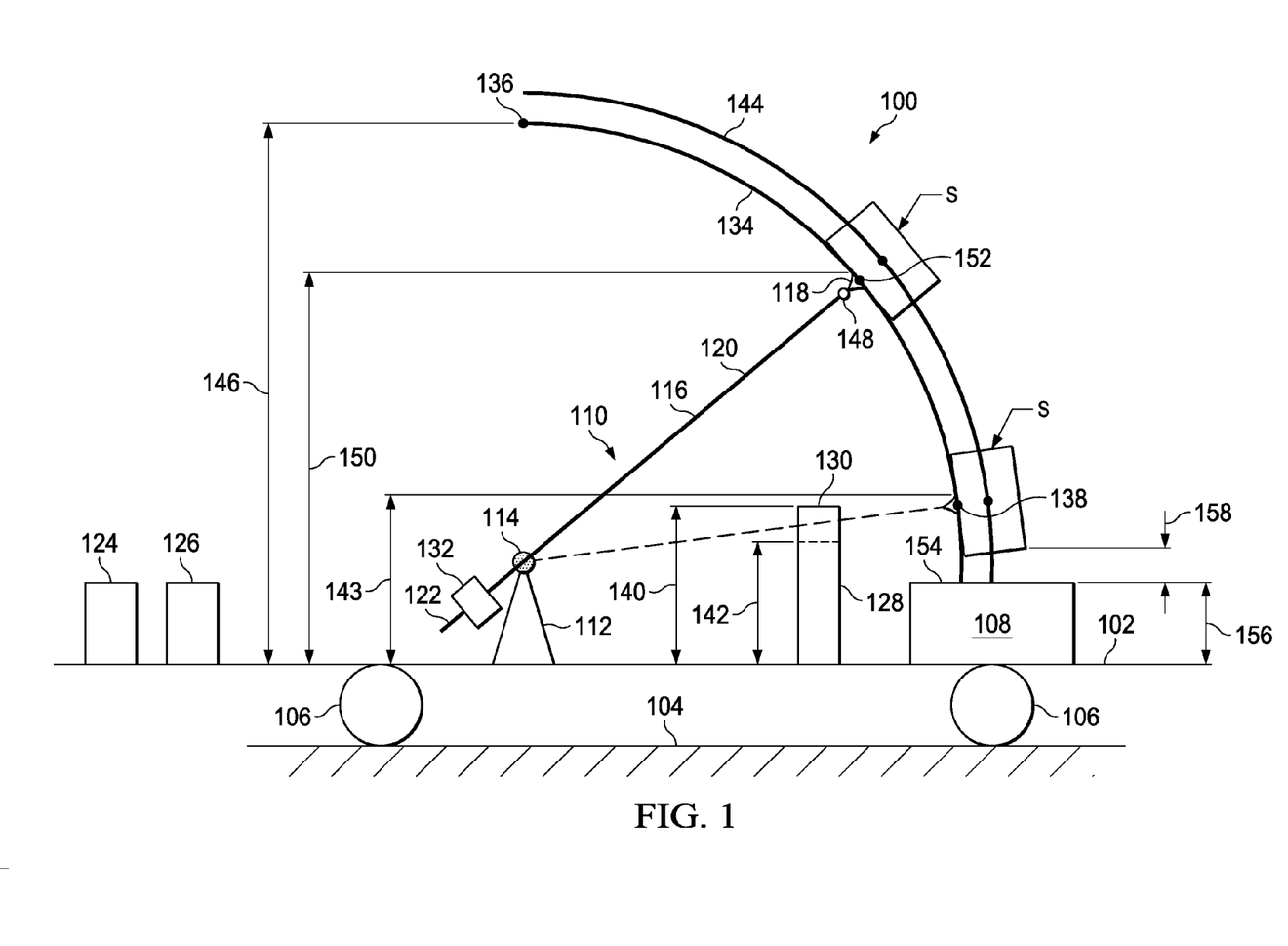
FIG. 1 is a schematic diagram of an impact testing system according to an embodiment of the disclosure.

Referring now to FIG. 1, a schematic diagram of an impact testing system 100 according to an embodiment of the disclosure is shown. The system 100 comprises a substantially planar base 102 supported atop a ground surface 104 by rollers 106. The system 100 further comprises a substantially block-shaped impact pad 108 and a delivery device 110. In some embodiments, each of the impact pad 108 and the delivery device 110 may be substantially anchored to the base 102. Most generally, the delivery device 110 comprises an anchor 112, a hinge 114, an arm 116, and a retainer 118. The anchor 112 may be configured to secure the hinge 114 relative to the base 102. The hinge 114 may be configured for attachment to and/or retention of the arm 116. As shown, the hinge 114 may comprise an axis of rotation located a greater offset distance from the base 102 as compared to an offset distance of an impact surface 154 of the pad 108 from the base 102.

In some embodiments, the arm 116 may be a substantially rigid beam hinged along a lengthwise axis of the beam so that the beam may be conceptualized as being segmented into a delivery segment 120 and a counter segment 122, each segment 120, 122 extending away from the hinge 114. At least one retainer 118 is carried by the delivery segment 120. The retainer 118 comprises a fluid pressure activated component, such as, but not limited to, a ported suction cup. As such the retainer 118 may be operated to remove fluid from a volume enveloped by the suction cup and alternately may be operated to introduce fluid to the volume enveloped by the suction cup. Accordingly, the retainer 118 may be operated to selectively retain a test specimen S, such as, but not limited to, a handheld mobile telecommunication device, by selectively controlling fluid pressure applied at the port of the suction cup of the retainer 118. The retainer 118, and hence the suction cup, may be configured to comprise dimensions, a range of capable retention force, a resiliency, a tackiness, and/or other features suitable for selectively retaining a variety of surfaces of a specimen S and for selectively retaining the specimen S in spite of a variety of potential kinetic forces that may tend to separate the specimen S from the retainer 118.

The system 100 further comprises a vacuum pump 124, a vacuum chamber 126, and a fluid piston 128. The vacuum pump 124 is selectively operable to remove fluid from the vacuum chamber 126 and/or the ported suction cup of the retainer 118. The vacuum chamber 126 serves to provide a source of relatively lower fluid pressure to the retainer 118. It will be appreciated that the system 100 comprises fluid conduits configured to interconnect the various fluid components of system 100. The fluid conduits may be configured to withstand a range of positive and negative fluid pressures without detrimental deformation and/or fatigue failure as necessary to provide the above-described selective retention of the test specimen S to the retainer 118. The piston 128 comprises an activation surface 130. Application of a sufficient impact force against the activation surface 130, in a direction toward the base 102 in the orientation shown, results in a positive fluid pressure pulse output from the piston 128. The piston 128 is configured to selectively provide a positive fluid pressure pulse output sufficient to overcome any substantially static relatively lower fluid pressure in the ported suction cup of the retainer 118. Additionally, the piston 128 may be configured to selectively provide a sufficient fluid flow to the suction cup of the retainer 118 to actively accelerate the test specimen S away from the retainer 118.

The counter segment 122 may carry an adjustable counterweight 132. The counterweight 132 may comprise multiple graduated parts of predetermined weights. In some embodiments, the counterweight 132 may be adjusted in position along the length of counter segment 122. It will be appreciated that adjustment of the parts of the counterweight 132 and/or the location of the parts of the counterweight 132 along the length of counter segment 122 may be used to calibrate the system 100.

Most generally, the arm 116 is configured for rotation about the axis of rotation of the hinge 114 in a constrained manner so that the retainer 118 may be generalized as being movable about the hinge 114 in a path 134, in some embodiments, between a highest point 136 and a lowest point 138. In some embodiments, the path 134 comprises a generally circular arc. The highest point 136 is referred to as such because that point represents a position of the arm 116 in which the arm 116 is oriented substantially normal relative to the base 102, thereby locating the retainer 118 at a maximum distance 146 from the base 102. The lowest point 138 is referred to as such because that point represents a minimum distance 148 from the base 102 of the retainer 118, a position of the arm 116 in which the arm 116 is positioned against a fully compressed piston 128. More specifically, referring to the position of the arm 116 shown in phantom lines, the delivery segment 120 of the arm 116 is shown in contact with the activation surface 130 of piston 128 thereby demonstrating that the piston 128 is selectively operable to comprise an uncompressed height 140 and a compressed height 142. In this disclosure, discussions that refer to the so-called compression of a piston 128 may, in some embodiments, be understood as referring to the above-described movement of the activation surface 130 so that the overall height of the piston 128 is at least temporarily reduced. It will further be understood that such compression of the piston 128 may result in compression and/or displacement of fluid within the piston and/or result in compression and/or displacement of fluid that is in fluid communication with the piston 128. Just as the retainer 118 may be moved along the path 134, the specimen S carried by the retainer 118 may be generalized as being similarly movable along a path 144 that is substantially concentric with the path 134.

In some embodiments, the system 100 may comprise a plurality of retainers 118. In embodiments comprising a plurality of retainers 118, it will be appreciated that multiple retainers 118 may be mounted to and/or carried on a bar comprising a lengthwise axis oriented substantially transverse to the lengthwise axis of the delivery segment 120. Additionally, the lengthwise axis of the optional bar for carrying a plurality of retainers 118 may be oriented substantially parallel to the base 102. As such, the multiple retainers 118 may be configured to rotate about the hinge 114 at substantially the same heights and/or offset distances from the base 102. Further, a pressure setting of the vacuum pump 124 and/or a stroke length or other configurable feature of the piston 128 may be adjusted to compensate for the additional retainers 118 and/or additional specimens S.

In some embodiments, a retainer 118 and/or an optional bar carrying a plurality of retainers 118 may be movable relative to the lengthwise axis of the delivery segment 120. Particularly, the retainer 118 may be joined to the delivery segment 120 by an articulation joint 148 so that the retainer 118 and any attached specimen S may be oriented in a variety of positions relative to the delivery segment 120. In some embodiments, the articulation joint 148 may provide substantially unlimited adjustment resolution, while in other embodiments, the adjustment resolution between possible positions provided by the articulation joint 148 may be stepwise and/or incremented in nature.

Figure 2:
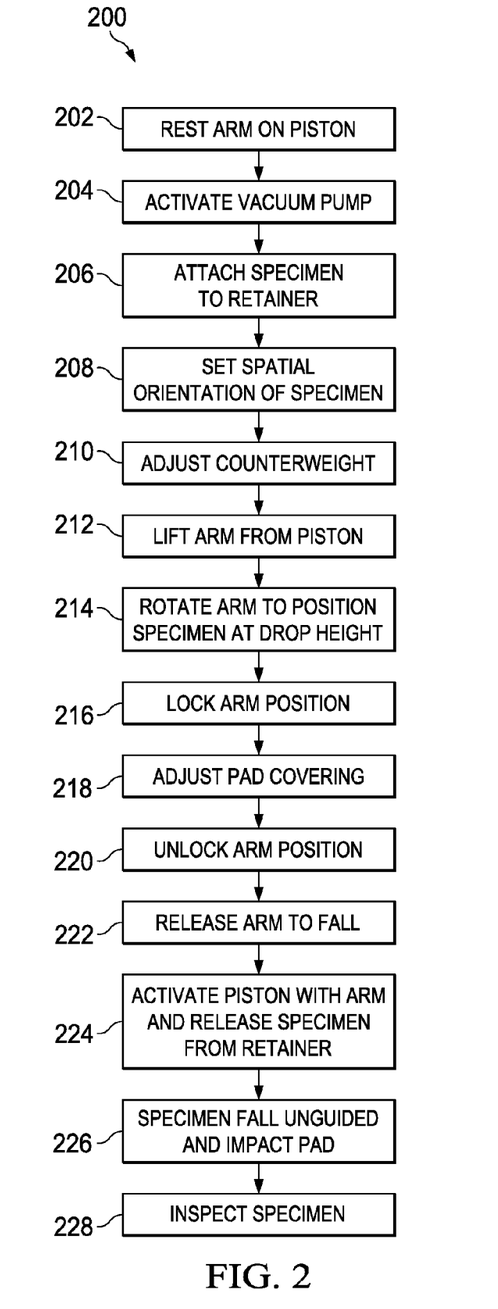
FIG. 2 is a flow chart of an impact testing method according to an embodiment of the disclosure.

Referring now to FIG. 2, a flow chart of a method 200 of impact testing a specimen is shown. Most generally, the system 100 may be operated to carry one or more specimens S along the path 144 and to release the specimens S from the retainers 118 so that the specimens S impact the pad 108 in a substantially predetermined orientation after travelling a relatively short distance (as compared to an overall distance traveled by the specimens S during the testing and prior to impacting the pad 108) substantially along the path 144 without connection to the retainers 118.

The method 200 may begin at block 202 by positioning the arm 116 so that the one or more retainers 118 are substantially located at the lowest point 138. As mentioned above, in this position, the delivery segment 120 will rest on piston 128 so that activation surface 130 is fully depressed and piston 128 comprises the compressed height 142.

At block 204, vacuum pump 124 may be activated to create a relatively lower fluid pressure within vacuum chamber 126 and to begin suction of fluid from a suction cup of retainer 118.

At block 206, a specimen S may be brought into contact with the suction cup of retainer 118 so that the specimen S is securely held.

At block 208, the articulation joint 148 may be operated to position the retainer 118 to hold the specimen S in substantially the same spatial orientation, but for overall vertical location, desired to be present upon impact of the specimen S with the pad 108. Some forethought in positioning the retainer and the specimen S may be given to anticipated tendencies of the specimen S to drift from the preset spatial orientation after and/or as a result of being released from the retainer 118 while moving along the path 144. In some embodiments, the specimen S may be a handheld mobile telecommunication device that may generally comprise a left side, a right side, a top side, a bottom side, a top right-front corner, a top right-rear corner, a top left-front corner, a top left-rear corner, a bottom right-front corner, a bottom right-rear corner, a bottom left-front corner, a bottom left-rear corner, a display surface, and a battery surface. In such an embodiment, the specimen S may be spatially oriented to ensure that a primary and/or first impact occurs on a selected one of the above listed features of the handheld mobile telecommunication device.

At block 210, the counterweight 132 may optionally be adjusted, thereby calibrating and/or recalibrating the system 100. For example, the counterweight 132 may be increased in mass and/or moved further away from the hinge 114 along the lengthwise axis of the counter segment 122.

At block 212, the arm 116 may be lifted from resting on the piston 128 and the piston 128 may be reset to raise the activation surface 130 until system 128 comprises the uncompressed height 142.

At block 214, the arm 116 may be rotated to locate the retainer 118 at a drop height 150 at which height the retainer 118 is located in an intermediate position at an intermediate point 152 along the path 134 between the lowest point 138 and the highest point 136. In some embodiments, the drop height 150 may comprise a value of about 0.25 meters to about 2 m, alternatively about 0.5 m to about 1.5 m, alternatively about 0.75 m to about 1.25 m, alternatively about 1 m. In some embodiments, the drop height 150 may comprise a value of about 0.025 m to about 4 m, alternatively about 0.25 m to about 3 m, alternatively about 1 m to about 2 m, alternatively about 1.25 m to about 1.75 m, alternatively about 1.5 m. In some embodiments, a value of the drop height 150 may be selected to emulate a distance from which a handheld mobile telecommunication device may likely be dropped, such as, but not limited to a height associated with a user's pocket or alternatively a height associated with a user's face.

In some embodiments, a graduated ruler and/or other measurement indicia may be fixed relative to the base 102 for use in determining a height of the retainer 118. Alternatively, indicia and/or other markings may be made at predetermined locations along the length of the delivery segment 120 and such indicia and/or other markings may be used in conjunction with rulers, grids, graduated lines, and such or any other suitable height indicator that is correlated to indicate the height of the retainer 118. Of course, in other embodiments, substantially similar retainer 118 heights may be achieved by appropriately measuring a height of a different location along the length of the delivery segment 120 and/or appropriately measuring a rotation angle of the arm 116. Regardless the manner in which the height of the retainer 118 is determined, it will be appreciated that knowledge of the specimen S dimensions may further provide knowledge of a height of the specimen S. In some cases, features of a specimen S may be concentrated on as a point of interest which must be raised to a particular height. For example, a specimen S may be raised so that a lowermost portion of the specimen S is located substantially 1 m relatively higher than the impact surface 154 of the pad 108. In any such case where a height of a particular component is required to be a particular distance above the pad 108, the pad 108 height 156 must be taken into account.

At block 216, the arm 116 may be temporarily locked into place.

At block 218, the pad 108 may be outfitted with an alternative covering and/or layer. For example, in some cases it may be appropriate to cover the otherwise substantially rigid and/or incompressible pad 108 (for example, but not limited to, a concrete pad 108) with a covering commonly encountered by specimen S when dropped during customary usage situations of the specimen S. For example, if the specimen S is a device often used in a hospital setting, the pad 108 may be outfitted and/or covered with a layer of linoleum tile substantially similar to the commonplace flooring material found in hospital settings.

At block 220, the arm 116 may be unlocked and again be free to rotate.

At block 222, the arm 116 may be released to fall freely. As the arm 116 rotates about the hinge 114, the retainer 118 and the specimen S travel along the paths 134, 144, respectively, and approach the pad 108.

At block 224, the delivery segment 120 of the arm 116 contacts the activation surface 130 of the piston 128 with force sufficient to begin compression of the piston 128. As the piston 128 is compressed, the piston 128 emits a positive fluid pressure pulse to the ported suction cup of the retainer 118. The positive fluid pressure pulse overcomes the relatively lower and/or vacuum pressure previously present within the ported suction cup 118. In some embodiments, the positive fluid pressure pulse may further provide a short-term fluid flow out through the ported suction cup of the retainer 118 so that a zone of relatively higher fluid pressure forms between the ported suction cup and the specimen S. Such a zone of relatively higher fluid pressure may have the effect of blowing and/or pushing the specimen S away from the suction cup. Regardless of the extent of the positive fluid pressure pulse, the result of the positive fluid pressure pulse is that the specimen S is no longer retained by the retainer 118.

At block 226, the delivery segment 120 may come to rest on the piston 128 while the specimen S continues to fall substantially along the path 144 toward the pad 108. In some embodiments, the specimen S substantially retains the spatial orientation previously set at block 208. The specimen S may fall unguided a so-called terminal distance 158 from the moment of release from the retainer 118 until the specimen S impacts the pad 108 and/or any optional coverings to the pad 108. In some embodiments, the terminal distance 158 may be about 1 cm to about 10 cm, alternatively about 2.5 cm to about 7.5 cm, alternatively about 5 cm. In other embodiments, the terminal distance 158 may be less than 1 cm or greater than 10 cm and selection of such terminal distance 158 may be a function of a speed with which a specimen S may successfully be released from a retainer 118.

At block 228, the specimen S may be retrieved, inspected, and/or further tested. In some embodiments, the specimen S may be repeatedly tested in the manner described above until a failure of the specimen S occurs or alternatively until a predetermined number of tests have been conducted on the specimen S.

Figure 3:
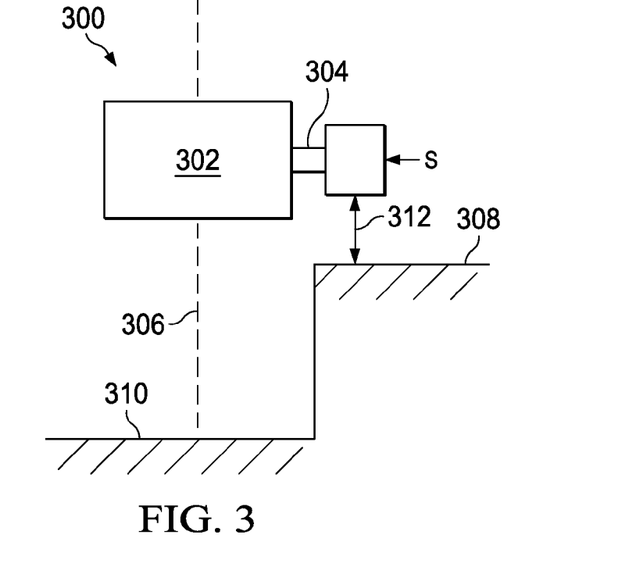
FIG. 3 is a schematic diagram of an impact testing system according to another embodiment of the disclosure.

Referring now to FIG. 3, a schematic diagram of an impact testing system 300 according to an embodiment of the disclosure is shown. The system 300 comprises a movable body 302 and a retainer 304 carried by the movable body 302. Most generally, the movable body 302 is configured to selectively travel along a space curve at least partially in response to a gravitational acceleration of the body 302. In some embodiments, the mass of the body 302 may be substantially greater than the mass of the specimen S. The body 302 may be caused to travel along a space curve 306, shown as a substantially vertical path, with the retainer 304 attached thereto and with the specimen S connected to the retainer 304 in a predetermined spatial orientation. In cases where the mass of the body 302 is substantially greater than the mass of the specimen S, the body 302 may substantially preserve a spatial orientation of the specimen S while the body 302 is falling because the body 302 is substantially more resistant to rotational changes as compared to the specimen S alone. The specimen S may travel toward a specimen impact surface 308 while the body 302 travels toward a body impact surface 310. In some embodiments, when the specimen S is a terminal distance 312 from the specimen impact surface 308, the retainer 304 may release the specimen S. As such, the specimen S may separate from the retainer 304. The specimen S may impact the impact surface 308 while the body 302 continues to move toward the body impact surface 310. In the manner described above, the specimen S may impact the specimen impact surface 308 with a predefined spatial orientation relative to the impact surface 308. In alternative embodiments, the body 302 may carry a plurality of retainers 304 thereby enabling the system 300 to test multiple specimens S at a time.

Figure 4:
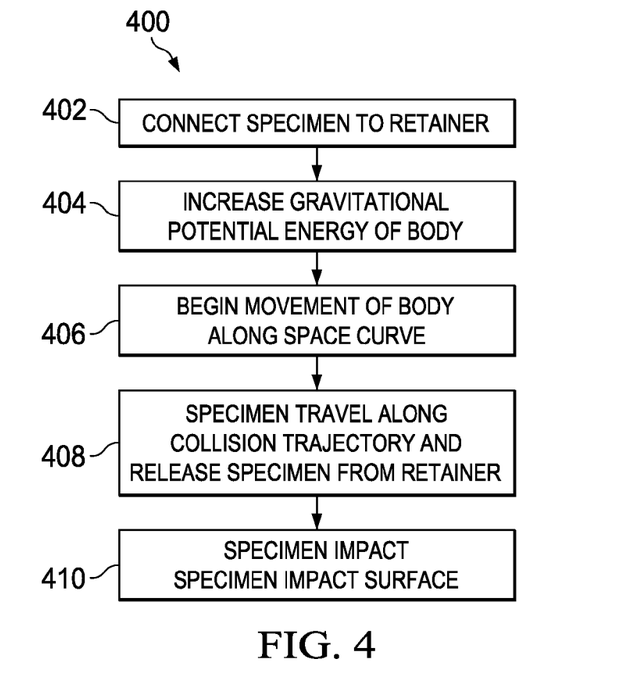
FIG. 4 is a flow chart of an impact testing method according to another embodiment of the disclosure.

Referring now to FIG. 4, a flow chart of a method 400 of impact testing a specimen is shown. At block 402, the method 400 may initiate by connecting a specimen S to the retainer 304 in a desired spatial orientation where the desired spatial orientation is selected knowing a space curve along which the body 302 will travel during the test. At block 404, any work necessary to provide a body 302 and/or an attached retainer 304 with gravitational potential energy may be performed. At block 406, the body 302 may be caused to begin travel along a known space curve. At block 408, the specimen S may be traveling along a trajectory that will result in a collision between the specimen S and the specimen impact surface 308. During such travel, the retainer 304 may release the specimen S at a terminal distance 312 above the specimen impact surface 308. At block 410, the specimen S may continue to travel along the trajectory until the specimen S impacts the specimen impact surface 308. During such travel and impact, the body 302 may continue to travel toward a body impact surface 310 and/or impact the body impact surface 310.

Figure 5:
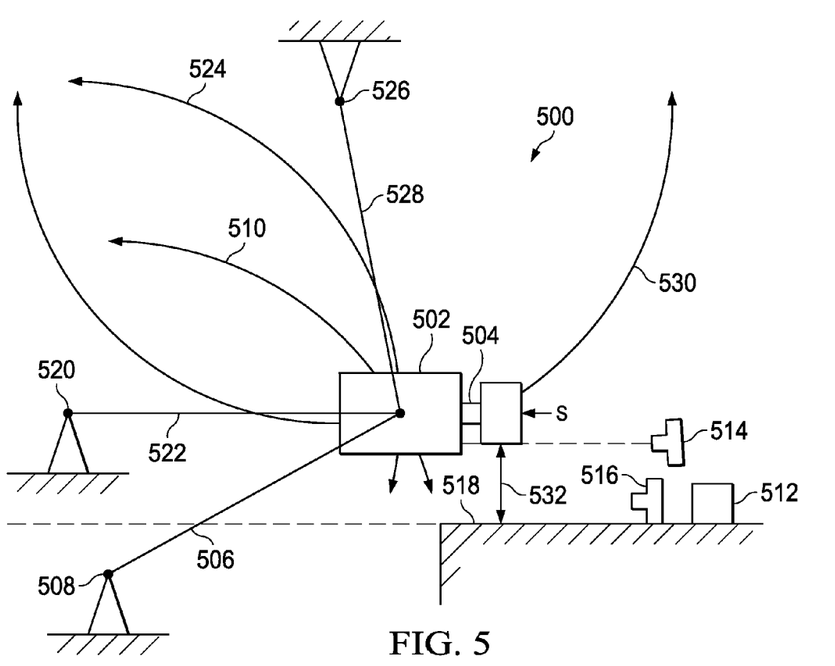
FIG. 5 is a schematic diagram of an impact testing system according to another embodiment of the disclosure.

Referring now to FIG. 5, a schematic diagram of an impact testing system 500 according to an embodiment of this disclosure is shown. The system 500 comprises a carrier 502, a retainer 504, a linkage 506, and a pivot 508. In some embodiments, the carrier 502 and the linkage 506 may together form a single component. However, in this embodiment, the carrier 502 is designated separately from the linkage 506 to illustrate that the linkage 506 may comprise one or more components that cooperate together to substantially allow movement of the carrier 502 along a path 510 about the pivot 508. In some embodiments, the path 510 may comprise a generally circular arc. The retainer 504 is configured to selectively retain a specimen S. More specifically, the retainer 504 may comprise a biased mechanism (for example, but not limited to, a spring biased mechanism), a magnetic retention mechanism, a suction mechanism, a geometric feature, and/or a material configured to retain connection between the retainer 504 and the specimen S until the retainer 504 is triggered to release the specimen S. In some embodiments, a computer 512 may be configured to control at least one of a movement of the linkage 506 and the carrier 502, a release of the specimen S from the retainer 504, and/or reception of a signal from an optical device 514 configured to monitor and/or report a location of the specimen S and/or a movable component of the system 500. The computer 512 may further be configured to receive user input from a human operable interface and then send control signals to the retainer 504 to cause the retainer 504 to adjust a spatial orientation of an attached specimen S and/or to move the linkage 506 so that the carrier 502 is relocated along the path 510. In some embodiments, the computer may cause activation of a high-speed camera 516 to capture video and/or photographs of the specimen S impacting an impact surface 518.

While linkage 506 is shown simply as a rod, alternative embodiments may comprise multi-part linkages and/or so-called active linkages. In some embodiments, an active linkage may comprise one or more gear connections between linkage components. In other embodiments, linkages may comprise mechanical dampening components, tension components, rotational components, and/or motorized components that may alter and/or control movement of the carrier 502. As such, in some embodiments, a linkage 506 may substantially affect motion of the carrier 502. For example, a linkage 506 may comprise components configured to increase or decrease acceleration and/or velocity of a carrier along the path 510. Still further, alternative embodiments may comprise a linkage that causes a carrier 502 to deviate from the path 510.

While the pivot 508 is located vertically lower than the impact surface 518, a pivot may be provided in other locations relative to the impact surface 518. In some embodiments, a pivot 520 may be located vertically higher than the impact surface 518. The pivot 520 may be configured to allow rotation of a linkage 522 and the carrier 502 about a path 524. In some embodiments, the path 524 may comprise a generally circular arc. In other embodiments, a pivot 526 may be located vertically higher than the impact surface 518 and a linkage 528 may generally hang from the pivot 526 that is generally located vertically higher than the linkage 528 and/or the carrier 502. The pivot 526 may generally allow rotation of the linkage 528 and/or the carrier 502 about a path 530. In some embodiments, the path 530 may comprise a generally circular arc. Still further, in some embodiments, the pivots 508, 520, 526 may comprise a ball and socket joint, a universal joint, and/or any other connection that allows the 502 to move in three dimensions along a generally spherical surface and/or spherical geometric sweep. In some embodiments of this disclosure, pivots may be assumed to present negligible friction. Of course, in some embodiments, combining such alternative connections between linkages and pivots, and considering that some linkages may be computer controlled active linkages, it will be appreciated that a carrier 502 may not be restricted to a simple geometrical path of movement, but rather, may be moved according to a computer generated complex path.

Regardless of the carrier 502 path provided by the pivots, linkages, and computer, the retainer 504 may nonetheless be controlled to selectively release the specimen S at a predetermined location and/or orientation relative to the impact surface 518. For example, the retainer 504 may simply be controlled to release the specimen S in response to the specimen S contemporaneously having both (1) a trajectory that would cause the specimen S to impact the impact surface 518 if released and (2) a height above the impact surface 518 equal to a terminal height 532.

In some embodiments, any one of the above-described impact testing systems may be configured to emulate a human's accidental dropping of a handheld mobile telecommunication device. It will be appreciated that the systems and methods disclosed herein are well suited for performing impact testing in both repeatable and random manners. For example, an impact test may be repeated with accuracy by repeatedly attaching specimens S to impact testing system 100 in substantially the same spatial orientation, dropping the arm 116 from a location with the specimens S at substantially the same height, and releasing the specimens S from the retainers 118 at substantially the same terminal height 158. Alternatively, an impact test may be made substantially random by purposefully randomizing at least one of a spatial orientation of the specimens S and/or a trajectory of the released specimens S. Of course, any of the embodiments disclosed herein may be configured to comprise multiple retainers and the use of such multiple retainers during testing clearly provides an increase in testing throughput as compared to impact testing a single specimen S at a time.

While the mechanisms by which fluid pistons and optical sensors generate a signal to cause retainers to release associated specimens may differ, the mechanisms each serve as a so-called trigger to initiate the release. Accordingly, the functionality of the fluid pistons, optical sensors, mechanical switches, and other devices allows the devices to be referred to more generally as triggers. A trigger may be configured to determine a height of one or more components of the systems disclosed herein and to thereafter generate a control signal intended to cause retainers to release specimens so the specimens can continue moving and later impact an impact surface.

In alternative embodiments of impact testing systems and methods, a carrier may integrally comprise features of a retainer. A method of impact testing a specimen may comprise attaching a specimen to a carrier. Next, the carrier may be moved relative to an impact surface in a manner configured to impart to the specimen a trajectory that would cause an impact between the specimen and the impact surface substantially at a known location on the specimen if the specimen were to be released from the carrier. Next, the carrier may release the specimen in a manner configured to impart to the specimen a trajectory that will cause an impact between the specimen and the impact surface substantially at a known location on the specimen and with a substantially known spatial orientation relative to the impact surface. Finally, the specimen may impact the impact surface at substantially a known location on the specimen and with a substantially known spatial orientation relative to the impact surface.

Figure 6:
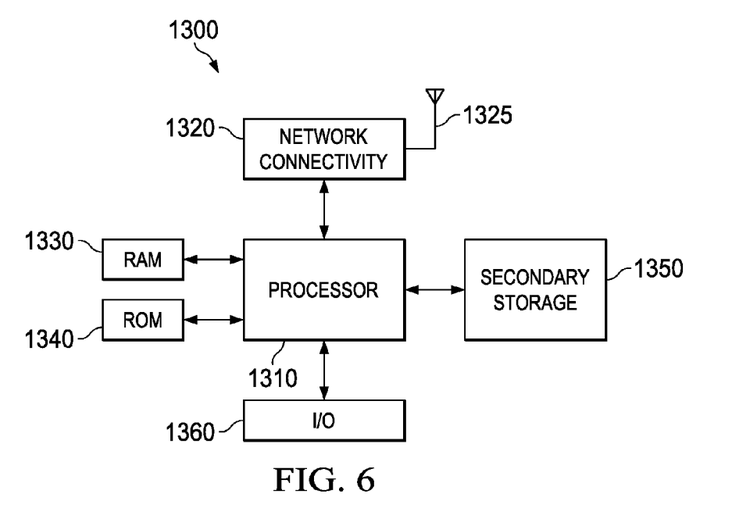
FIG. 6 is a representation of a general-purpose processor (e.g., electronic controller or computer) system suitable for implementing the embodiments of the disclosure.

FIG. 6 illustrates a typical, general-purpose processor (e.g., electronic controller or computer) system 1300 that includes a processing component 1310 suitable for implementing one or more embodiments disclosed herein. In addition to the processor 1310 (which may be referred to as a central processor unit or CPU), the system 1300 might include network connectivity devices 1320, random access memory (RAM) 1330, read only memory (ROM) 1340, secondary storage 1350, and input/output (I/O) devices 1360. In some cases, some of these components may not be present or may be combined in various combinations with one another or with other components not shown. These components might be located in a single physical entity or in more than one physical entity. Any actions described herein as being taken by the processor 1310 might be taken by the processor 1310 alone or by the processor 1310 in conjunction with one or more components shown or not shown in the drawing.

The processor 1310 executes instructions, codes, computer programs, or scripts that the processor 1310 might access from the network connectivity devices 1320, RAM 1330, ROM 1340, or secondary storage 1350 (which might include various disk-based systems such as hard disk, floppy disk, optical disk, or other drive). While only one processor 1310 is shown, multiple processors may be present. Thus, while instructions may be discussed as being executed by a processor, the instructions may be executed simultaneously, serially, or otherwise by one or multiple processors. The processor 1310 may be implemented as one or more CPU chips.

The network connectivity devices 1320 may take the form of modems, modem banks, Ethernet devices, universal serial bus (USB) interface devices, serial interfaces, token ring devices, fiber distributed data interface (FDDI) devices, wireless local area network (WLAN) devices, radio transceiver devices such as code division multiple access (CDMA) devices, global system for mobile communications (GSM) radio transceiver devices, worldwide interoperability for microwave access (WiMAX) devices, and/or other well-known devices for connecting to networks. These network connectivity devices 1320 may enable the processor 1310 to communicate with the Internet or one or more telecommunications networks or other networks from which the processor 1310 might receive information or to which the processor 1310 might output information.

The network connectivity devices 1320 might also include one or more transceiver components 1325 capable of transmitting and/or receiving data wirelessly in the form of electromagnetic waves, such as radio frequency signals or microwave frequency signals. Alternatively, the data may propagate in or on the surface of electrical conductors, in coaxial cables, in waveguides, in optical media such as optical fiber, or in other media. The transceiver component 1325 might include separate receiving and transmitting units or a single transceiver. Information transmitted or received by the transceiver 1325 may include data that has been processed by the processor 1310 or instructions that are to be executed by processor 1310. Such information may be received from and outputted to a network in the form, for example, of a computer data baseband signal or signal embodied in a carrier wave. The data may be ordered according to different sequences as may be desirable for either processing or generating the data or transmitting or receiving the data. The baseband signal, the signal embedded in the carrier wave, or other types of signals currently used or hereafter developed may be referred to as the transmission medium and may be generated according to several methods well known to one skilled in the art.

The RAM 1330 might be used to store volatile data and perhaps to store instructions that are executed by the processor 1310. The ROM 1340 is a non-volatile memory device that typically has a smaller memory capacity than the memory capacity of the secondary storage 1350. ROM 1340 might be used to store instructions and perhaps data that are read during execution of the instructions. Access to both RAM 1330 and ROM 1340 is typically faster than to secondary storage 1350. The secondary storage 1350 is typically comprised of one or more disk drives or tape drives and might be used for non-volatile storage of data or as an over-flow data storage device if RAM 1330 is not large enough to hold all working data. Secondary storage 1350 may be used to store programs or instructions that are loaded into RAM 1330 when such programs are selected for execution or information is needed.

The I/O devices 1360 may include liquid crystal displays (LCDs), touch screen displays, keyboards, keypads, switches, dials, mice, track balls, voice recognizers, card readers, paper tape readers, printers, video monitors, transducers, sensors, or other well-known input or output devices. Also, the transceiver 1325 might be considered to be a component of the I/O devices 1360 instead of or in addition to being a component of the network connectivity devices 1320.

Some or all of the I/O devices 1360 may be substantially similar to various components depicted in the previously described Figures.

In some embodiments of the disclosure, a testing system is provided that comprises a retainer configured to selectively retain a specimen and a carrier configured to selectively carry the retainer along an at least partially predefined space curve from a first point along the space curve to a second point along the space curve, wherein a gravitational potential energy of the retainer at the first point is greater than a gravitational potential energy of the retainer at the second point. The retainer is configured to release the specimen in response to the retainer moving to a location that provides the retainer a predetermined gravitational potential energy.

In some embodiments of the disclosure, a method of impact testing is provided that comprises providing a movable body configured to selectively move along an at least partially predefined space curve, providing an impact surface, attaching a specimen to the body in a substantially predefined spatial orientation relative to the body, and moving the body along the space curve wherein the moving decreases a distance between the specimen and the impact surface. The method further comprises releasing the specimen from the body wherein the releasing is configured to cause an impact between the specimen and the impact surface and impacting the specimen against the impact surface in a predefined spatial orientation relative to the impact surface.

In some embodiments of the disclosure, an impact testing system is provided that comprises an impact surface, an arm rotatably connected to a hinge, at least one retainer attached to the arm along a length of the arm, the retainer being configured to selectively retain a specimen, and a trigger in communication with the at least one retainer, the trigger being configured to cause the at least one retainer to discontinue retention of the specimen in response to the occurrence of a predetermined condition.

While several embodiments have been provided in the present disclosure, it should be understood that the disclosed systems and methods may be embodied in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A testing system, comprising:
   a retainer configured to selectively retain a specimen;
   an arm configured to selectively carry the retainer along an at least partially predefined space curve from a first point along the space curve to a second point along the space curve, wherein a gravitational potential energy of the retainer at the first point is greater than a gravitational potential energy of the retainer at the second point; and
   a fluid piston in fluid communication with the retainer, wherein when the fluid piston is compressed by the arm moving along the space curve, the retainer is configured to release the specimen.

2. The testing system of claim 1, wherein the retainer is selectively adjustable in space relative to the arm.

3. The testing system of claim 1, wherein the space curve comprises a substantially circular arc.

4. The testing system of claim 1, wherein the arm is constrained along a lengthwise axis of the arm to selectively rotate about a pivot point.

5. The testing system of claim 1, wherein the retainer comprises a suction cup.

6. The testing system of claim 1, wherein the space curve is substantially coincident with a spherical surface.

7. The testing system of claim 1, wherein the fluid piston is compressed by a force exerted by the arm.

8. The testing system of claim 1, wherein a point along the space curve at which the retainer releases the specimen is based on a height of the fluid piston.

9. A method of impact testing, comprising:
   providing a movable body comprising an arm and a retainer to selectively move along an at least partially predefined space curve;
   providing an impact surface;
   providing a fluid piston in fluid communication with the retainer;
   attaching a specimen to the retainer in a substantially predefined spatial orientation relative to the arm;
   moving the arm along the space curve, wherein the moving decreases a distance between the specimen and the impact surface;
   releasing the specimen from the retainer when the fluid piston is compressed by the arm moving along the space curve, wherein the releasing is configured to cause an impact between the specimen and the impact surface; and
   impacting the specimen against the impact surface in a predefined spatial orientation relative to the impact surface.

10. The method of claim 9, wherein the at least partially predefined space curve comprises a substantially circular arc.

11. The method of claim 9, wherein the attaching the specimen to the retainer and the releasing the specimen from the retainer comprise attaching the specimen to a suction cup and releasing the specimen from the suction cup, respectively.

12. The method of claim 9, wherein the arm is configured for rotation about a hinge.

13. The method of claim 9, wherein the releasing the specimen is performed in response to the specimen being located a predefined distance from the impact surface.

14. The method of claim 9, wherein the moving the arm along the space curve comprises reducing a gravitational potential energy of the retainer.

15. The method of claim 9, wherein the specimen is a handheld mobile telecommunication device.

16. An impact testing system, comprising:
   an impact surface;
   an arm rotatably connected to a hinge;
   at least one retainer attached to the arm, the retainer being configured to selectively retain a specimen; and
   a fluid piston in fluid communication with the at least one retainer, wherein when the fluid piston is compressed by the arm, the retainer is configured to discontinue retention of the specimen.

17. The system of claim 16, wherein the at least one retainer comprises a ported suction cup.

18. The system of claim 16, wherein the fluid piston is configured to be compressed by the arm when the retainer is located at a predetermined distance vertically above the impact surface.

19. The system of claim 16, wherein the arm is configured to rotate the retainer from a location of about one meter vertically higher than the impact surface to a location of about five centimeters vertically higher than the impact surface prior to the discontinuation of the retention.

20. The system of claim 16, further comprising:
- a counterweight carried by the arm, the counterweight being configured to affect a kinetic rotation of the arm about the hinge.

* * * * *